United States Patent [19]

Kelman

[11] Patent Number: 5,190,552
[45] Date of Patent: Mar. 2, 1993

[54] SLOTTED TUBE INJECTOR FOR AN INTRAOCULAR LENS

[76] Inventor: Charles D. Kelman, 721 Fifth Ave., New York, N.Y. 10022

[21] Appl. No.: 830,693

[22] Filed: Feb. 4, 1992

[51] Int. Cl.⁵ .............................................. A61B 17/00
[52] U.S. Cl. .................................... 606/107; 606/108
[58] Field of Search ................. 606/107, 108; 604/15, 604/16, 17, 18, 311, 232, 233; 623/6

[56] References Cited

U.S. PATENT DOCUMENTS

| | | | |
|---|---|---|---|
| 4,681,102 | 7/1987 | Bartell | 606/107 X |
| 4,715,373 | 12/1987 | Mazzocco et al. | 606/107 |
| 4,836,201 | 6/1989 | Patton et al. | 606/107 |
| 4,862,885 | 9/1989 | Cumming | 606/107 |
| 4,934,363 | 6/1990 | Smith et al. | 606/107 |
| 4,957,505 | 9/1990 | McDonald | 606/107 X |
| 5,123,905 | 6/1992 | Kelman | 606/107 |

Primary Examiner—Peter A. Aschenbrenner
Attorney, Agent, or Firm—Darby & Darby

[57] ABSTRACT

An injector formed of a slotted tube is partially inserted via its front end in a minimum size eye incision to inject a temporarily folded intraocular lens having opposed haptics extending from its periphery, into the eye without stressing the incision. Holding and locking mechanisms serve to fold the lens into the tube rear end with the haptics protruding from the tube slot so as not to be jammed in the tube, and to unfold the lens out of the tube front end in the eye for release, all in controlled manner, and so as to avoid patient trauma from stress on the incision or contact of the unfolding lens with the inner wall of the cornea or other eye parts.

13 Claims, 3 Drawing Sheets

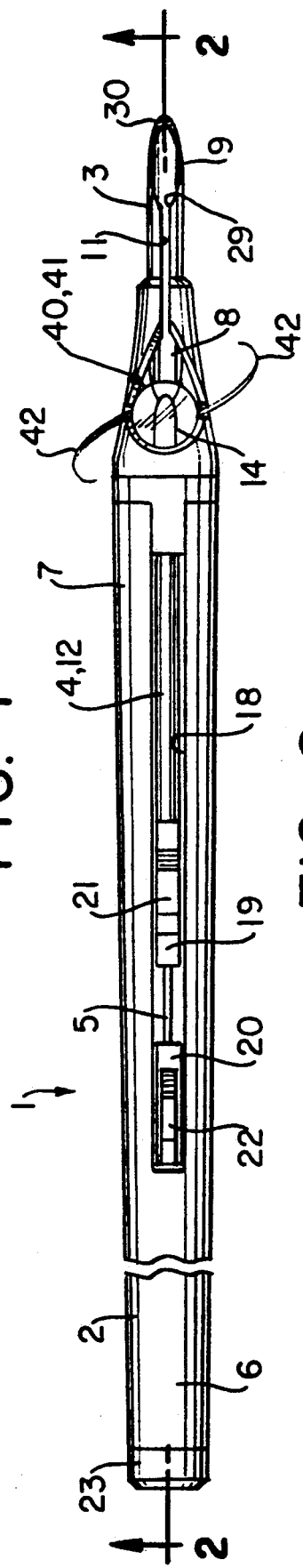
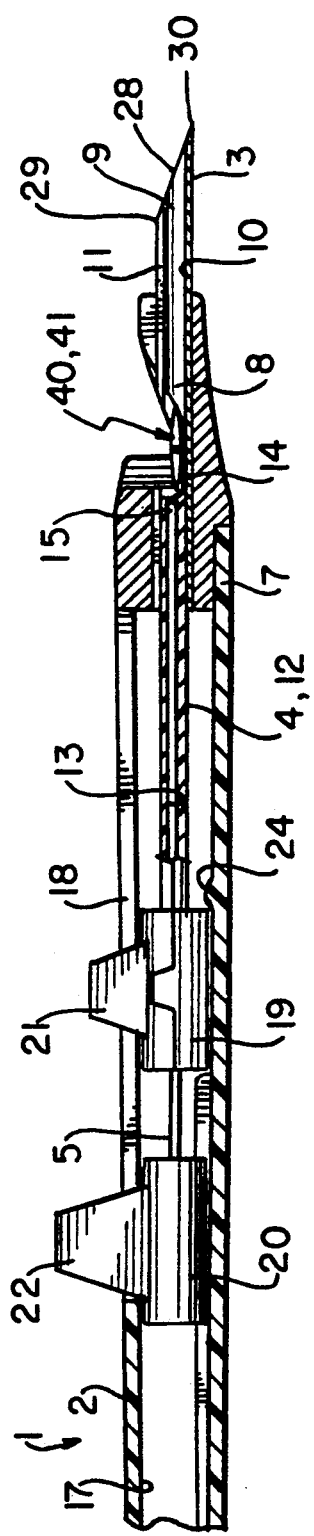

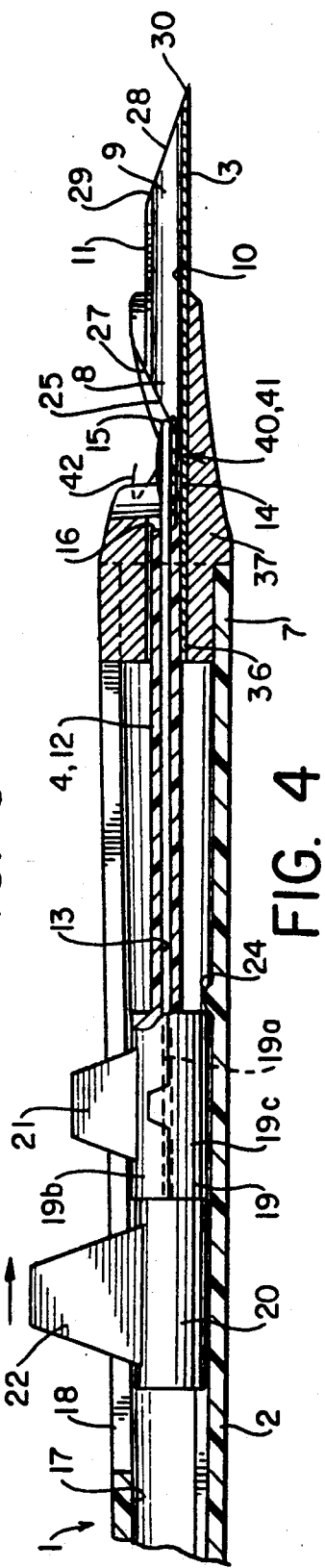
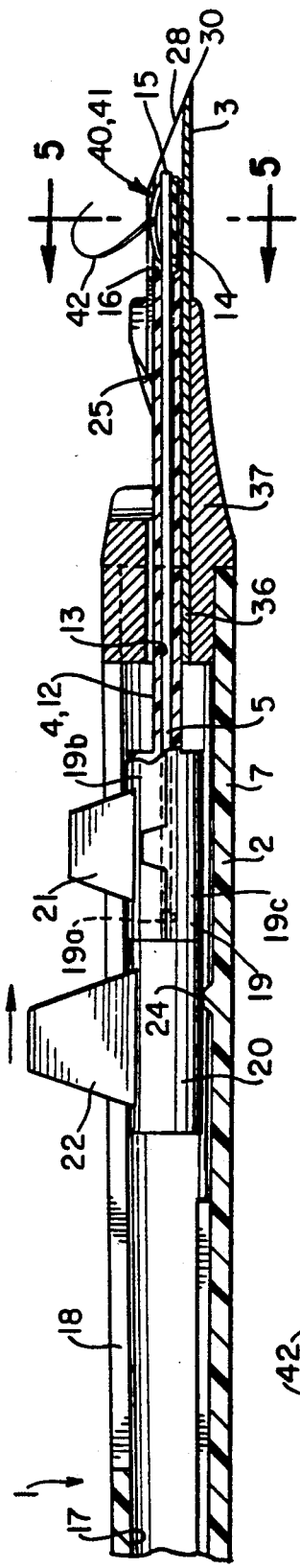
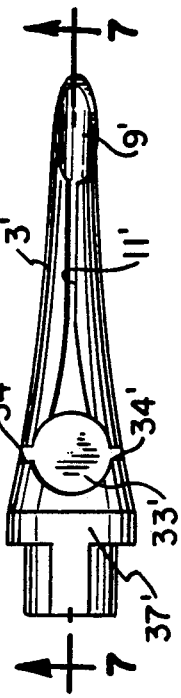
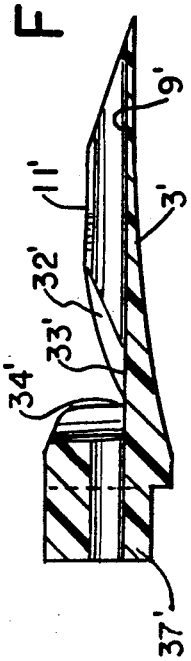
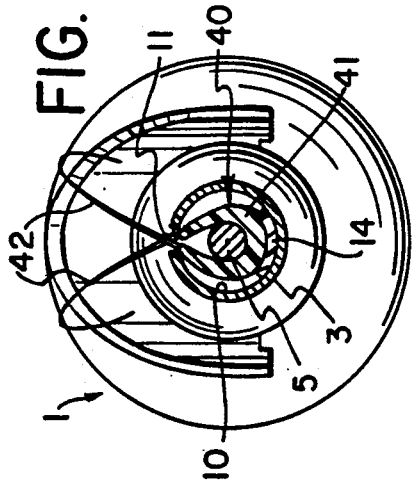

SLOTTED TUBE INJECTOR FOR AN INTRAOCULAR LENS

CROSS REFERENCE TO RELATED APPLICATION

This application is related to the subject matter disclosed and claimed in applicant's copending U.S. application Ser. No. 712,357 filed Jun. 7, 1991, now U.S. Pat. No. 5,123,905 entitled INTRAOCULAR LENS INJECTOR.

FIELD AND BACKGROUND OF THE INVENTION

The present invention relates to a slotted tube injector for an intraocular lens, and more particularly to a slotted tube for partial insertion in a minimum size incision to inject into the eye a temporarily folded, i.e. deformable, lens with opposed haptics, and means to fold the lens into the tube so that the haptics protrude from the tube slot, and to unfold the lens out of the tube in the eye for release, in controlled manner.

In eye surgery for treating conditions such as natural eye lens cataracts, a common procedure is to remove the cataracted lens through an incision in the cornea of the eyeball, and replace it by an artificial intraocular lens. The intraocular lens, typically 6 mm in diameter, is usually temporarily resiliently deformable, i.e. foldable into generally cylindrical shape, by curling, etc., to reduce its girth, and while kept folded is inserted through a corneal incision, typically 3.5-4 mm long, to minimize patient trauma. The lens has a lens body or optic, e.g. of soft material such as silicone, with normally stiffer resiliently deformable position fixation means or haptics, e.g. of polypropylene, extending therefrom to seat the lens in the eye.

The haptics must be kept in stable relation to the folded lens body during insertion into the eye so as to pass without difficulty through the incision. Once inserted, unfolding the lens body and haptics in the confined space at the implantation site must be controlled to avoid patient trauma from contact of these expanding mechanical elements with the inner wall of the cornea or other eye parts. Inserting the folded lens into an eye so as to minimize patient trauma is very difficult. A tool is needed to hold and insert the folded lens, requiring an incision large enough to accommodate both. Often, a separate retainer keeps the lens folded, so that the inserted retainer and tool clutter the eye interior during lens unfolding, after which the tool and retainer must be retrieved via the incision.

U.S. Pat. No. 4,573,998 to Mazzocco shows tools to insert a deformable lens into the eye by pushing, stretching, ejecting or compressing action. On insertion, the lens and/or tools grossly contact the eye incision, and the lens must be released carefully to keep it from injuring internal eye parts as it expands.

U.S. Pat. No. 4,906,247 to Fritch shows a deformable lens held folded by forceps inserted in a stretchable plastic tube so as to stretch the tube diameter and squeeze the tube around the folded lens like a mitten. On insertion via an incision into the eye, the forceps must release the lens carefully to keep it from injuring internal eye parts as it expands.

U.S. Pat. No. 4,911,714 to Poley shows a deformable lens held folded by sutures connecting apertures on opposed edges of the lens, or by integral lock means or adhesive on such edges, for insertion by a first tool through a first incision into the eye. A second tool inserted through a second incision is used to cut and remove the sutures, unlock the lock means or break the adhesive bond while the first tool holds the lens to keep it from injuring internal eye parts as it expands.

U.S. Pat. No. 4,917,680 to Poley shows a deformable lens held folded by a severable retainer or band for insertion by a first tool through a first incision into the eye. A second tool inserted through a second incision is used to sever and remove the band while the first tool holds the lens to keep it from injuring internal eye parts as it expands.

U.S. Pat. No. 4,976,716 to Cumming shows an injector having inner and outer tubes, and a plunger in the inner tube, for a deformable lens with leading and trailing haptics. Two flexible, widely diverging, inner fingers integral with the inner tube front are notched near their free ends to form bendable tips. Two rigid outer fingers, pivoted to the outer tube front, lock the inner fingers in narrower diverging state for retracting the inner tube in the outer tube so that only its tips protrude. Jaws of a loader squeeze and fold the lens between the inner fingers so that the leading haptic protrudes from their narrower diverging tips, and then the outer fingers are locked and the leading haptic and diverging tips inserted in the eye incision.

A drive moves the inner tube and plunger forwardly of the outer tube for the inner finger notches to clear the incision and the stored force of the folded lens to bend the inner finger tips outwardly of their widely diverging position to unfold the lens partially. The drive then moves the plunger for pushing the lens beyond the inner finger tips to unfold it completely. A return spring retracts the plunger and inner tube from the incision. The unit is complex, costly and cumbersome to operate, and its diverging fingers stress the incision or require use of a larger incision. As the fingers do not surround the folded lens, but only hold its diametrically opposed girth portions, the outwardly projecting girth portions therebetween can contact and stress the incision and inner cornea wall during the insertion procedure.

U.S. Pat. No. 4,836,201 to Patton et al shows an injector with a tubular tip in which an outer curlable petal and inner shaft having a front finger extend and retract. A deformable lens having leading and trailing haptics is lodged between the extended uncurled petal and finger with its trailing haptic at the petal rear and leading haptic extending from the petal front. The petal and finger retract to curl the lens in the petal while the leading haptic protrudes from the tubular tip. On inserting the tip in an eye incision, the petal and shaft extend to uncurl the lens, and the petal retracts from the finger to release the lens. The unit is complex and the trailing haptic obviously jams at the petal and tip during retraction and extension action.

An injector made by Allergen Inc., known as "The Prodigy," has a tubular tip inserted in an eye incision to inject a folded lens into the eye, but has no means to control lens unfolding.

U.S. Pat. No. 940,519 to Eastman shows an inserter tube with a slot from its open end almost to its closed end to load a tampon in the open end by a cord pulled along the slot, for ejection by a plunger. The tampon remains unfolded throughout.

U.S. Pat. No. 2,351,836 to Popper shows an inserter tube with a slot from one open end to the other to load a tampon by a cord pulled along the slot. On insertion in the vagina, the tube is peeled away at its slot to remove it from the tampon. Also shown is a tube slidably holding a prefolded tampon seated in a detainer well having a tab protruding from a slot spaced from the tube ends. On insertion, the tab is held to immobilize the well and the tube retracted to unfold the tampon partly from the well to engage the vaginal walls. The well undesirably tends to carry the tampon outwardly with it as it is removed with the tube.

It is desirable to insert a temporarily folded intraocular lens via a minimum size incision into the eye by an instrument that does not unduly stress or traumatize the incision, permitting controlled gradual lens injection and unfolding in the eye to avoid incision trauma from such stress or contact of the unfolding lens with the cornea inner wall or other eye parts.

SUMMARY OF THE INVENTION

It is an object of the invention to overcome prior art drawbacks and to provide an injector having a slotted tube for partial insertion in a minimum size incision to inject into the eye a temporarily folded, i.e. deformable, intraocular lens having opposed seating haptics, and means to fold the lens into the tube so that its haptics protrude from the tube slot during insertion, and to unfold the lens out of the tube in the eye for release, all in controlled manner to avoid lens jamming in the tube and patient trauma from stress on the incision or contact of the unfolding lens with the cornea inner wall or other eye parts.

It is another object of the invention to provide such an injector of structurally simple parts, readily fabricated at relatively low cost, and preferably disposable.

According to the invention, a slotted tube injector is provided for partial insertion in a minimum size eye incision to inject into the eye a temporarily folded intraocular lens having generally opposed seating haptics extending from the lens periphery. The injector has a longitudinal support forwardly terminating in a tube, plus lens holding and locking means.

The tube has a rearwardly facing loading end and a forwardly facing insertion end interconnected by a through bore for containing the folded lens. A slot extending from the loading end to the insertion end communicates the bore with the tube exterior to permit the haptics to protrude from the folded lens in the bore. The insertion end is insertable in the incision.

The holding and locking means are arranged on the support for movement relative to the tube and serve to load and lock the lens in unfolded state thereon at the loading end, and to move the lens into the loading end for controlled folding of the lens into the bore and locating of the haptics in the slot so as to protrude to the exterior. On inserting the insertion end in the incision with the haptics passing through the incision protruding from the tube, said means serve to move the lens out of the insertion end for controlled lens unfolding out of the bore and return of the lens and haptics to unfolded state thereon, and then to unlock the lens for controlled release in the eye.

Gradually constricting guide means may be provided at the loading end to aid the controlled gradual lens folding into the bore and haptics locating in the slot. The constricting means may be defined by an inclined loading end that tapers upwardly and inwardly along an incline from a distal longitudinal point peripherally remote from the slot to a proximate longitudinal point peripherally at the slot. Also, gradually expanding guide means may be provided at the insertion end to aid the controlled gradual lens unfolding out of the bore and lens and haptics return to unfolded state. The expanding means may be defined by an inclined insertion end that tapers downwardly and outwardly along an incline from a proximate longitudinal point peripherally at the slot to a distal longitudinal point peripherally remote from the slot. The inclined insertion end desirably defines a pointed tip for insertion in the eye incision.

The holding and locking means are desirably formed of a holding sled and locking rod arranged on the support for movement relative to the tube to load the unfolded lens on the sled and lock it thereto by the rod at the loading end. Moving the sled and rod into the loading end folds the lens and locates the protruding haptics in the tube slot. On insertion in the incision, the sled and rod move out of the insertion end to unfold the lens and return it and the haptics to unfolded state, and the rod moves away from the sled to unlock and release the lens.

Initially, the sled is at a loading position at the loading end to load the unfolded lens thereon, and the rod is at a retracted position and moves to the loading position to lock the lens to the sled. They then move from the loading position into the loading end to a contained position in the tube for said lens folding and haptics locating. On inserting the insertion end in the incision, the sled and rod move from the contained position out of that end to an exposed position for said lens unfolding and lens and haptics return to unfolded state. Then, the rod alone moves away from the sled to unlock and release the lens.

Opposed gradually constricting guide surfaces may be formed at the loading end to guide opposing peripheral portions of the lens gradually toward each other and conformingly against and into the loading end to fold the lens during movement into that end. A breech recess may be defined in the support at the guide surfaces to locate the unfolded lens on the sled, with opposed grooves formed at the recess to receive and locate the opposed haptics in a direction crosswise of the slot to permit the guide surfaces to guide the haptics in predetermined orientation gradually toward each other and in turn longitudinally inwardly into the slot during lens movement into the loading end.

In one form, the sled has a longitudinal body with a rearward channel slidably receiving the rod coaxially to the tube bore, and a forward lens loading platform. The rod has a forward tip for overlying registry with the platform. The platform is transversely offset from the channel a distance corresponding substantially to the unfolded lens thickness to enable the tip to register with the platform to lock the lens therebetween for folding the lens generally coaxially around the tip as a core on moving into the loading end. The platform may have a shoulder to contact the lens periphery to prevent longitudinal lens displacement relative to the sled during their movement through the tube.

Movement control means may be provided to control conjoint movement of the sled and rod relative to the tube and individual movement of the rod relative to the sled and tube.

BRIEF DESCRIPTION OF THE DRAWINGS

Other objects of the invention will become apparent from the within specification and accompanying drawings, in which:

FIG. 1 is a top view of a slotted tube injector according to the invention, holding an unfolded intraocular lens;

FIG. 2 is a sectional view taken on line 2—2 of FIG. 1, showing the rod retracted from the sled;

FIG. 3 is a view like FIG. 2, but showing the rod locking the lens on the sled;

FIG. 4 is a view like FIG. 3, but showing the sled, rod and folded lens in the tube and the haptics protruding from its slot;

FIG. 5 is a cross sectional view taken on line 5—5 of FIG. 4, showing the lens in the tube bore and the protruding haptics;

FIG. 10 is a top view of a modified slotted tube form; and

FIG. 11 is a sectional view taken on line 11—11 of FIG. 10.

DESCRIPTION OF THE PREFERRED EMBODIMENTS

Figure 6:
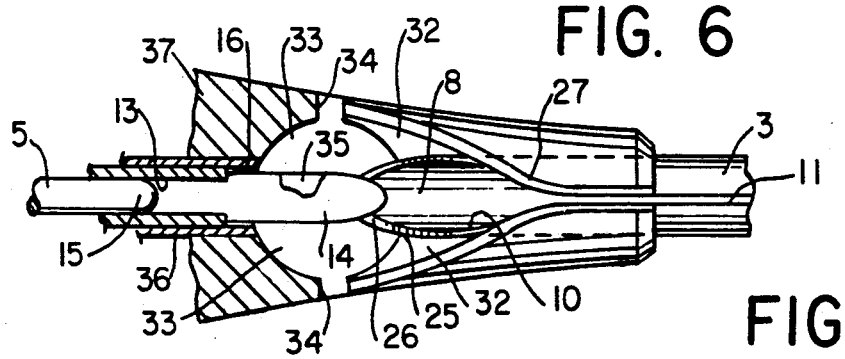
FIG. 6 is a partial top view of the tube loading end.

Referring to the drawings, and initially to FIGS. 1-9, a slotted tube injector 1 is shown according to an embodiment of the invention for partial insertion in a minimum size incision to inject into the eye a temporarily folded intraocular lens 40.

Lens 40 is conventional, having a temporarily foldable, i.e. resiliently deformable, optic or lens body 41 and a pair of generally diametrically opposed resiliently deformable position fixation means or haptics 42 to seat the lens in the eye. Lens 40 is foldable into a compact, e.g. cylindrical, shape of reduced girth, facilitating insertion through a minimum size incision into the eye, and unfolds to original undeformed state.

Injector 1 includes a longitudinal support 2 forwardly terminating in a hollow open ended, slotted longitudinal tube 3, and holding and locking means formed of a longitudinal lens holding sled 4 and a cooperating longitudinal lens locking rod 5.

Support 2 has a rear portion 6 serving as a handle for the surgeon and a front portion 7 at which tube 3 is located. Tube 3 has a rearwardly facing or rear loading end 8 and a forwardly facing or front insertion end 9 that is insertable in the eye incision. Ends 8 and 9 are interconnected by a longitudinal through bore 10 for containing lens 40 in folded state. A continuous longitudinal central top slot 11 extending from end 8 to end 9 communicates bore 10 with the tube exterior. Slot 11 is generally parallel to bore 10 and permits haptics 42 to protrude freely to the tube exterior from lens 40 when folded in bore 10.

Figure 7:
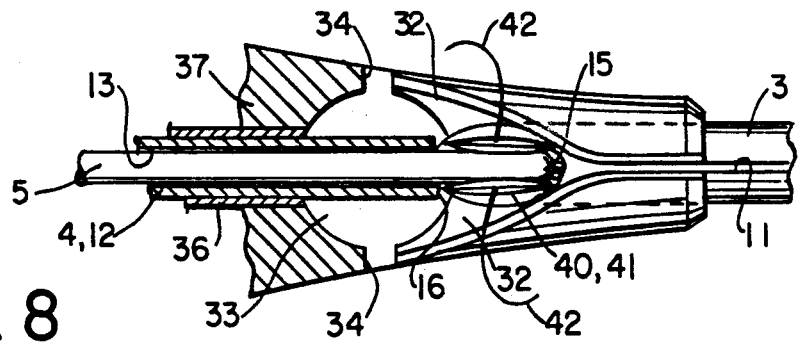
FIG. 7 is a view like FIG. 6, but showing the folding of the lens into the tube loading end.
Figure 8:
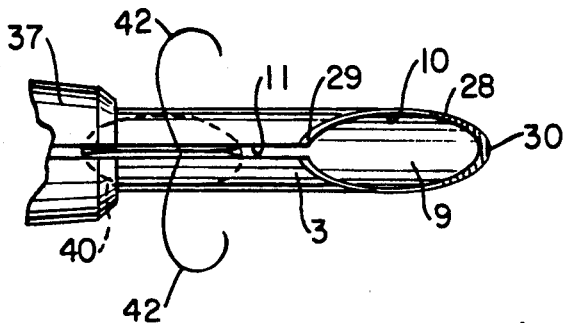
FIG. 8 is a partial top view of the tube insertion end showing the folded lens therein.

Sled 4 has a longitudinal body 12 with a rearward channel 13 longitudinally slidably receiving rod 5 coaxially to bore 10, and a forward platform 14 to load lens 40 in unfolded state thereon (FIGS. 1-2 and 6). Rod 5 has a forward tip 15 for overlying registry with platform 14. Platform 14 is transversely offset from channel 13 at a shoulder 16 by a distance corresponding substantially to the thickness of lens 40 when unfolded. This enables tip 15 to move into registry with platform 14 to lock lens 40 therebetween (FIG. 3), for folding the lens generally coaxially around tip 15 as a core (FIGS. 5), during movement into loading end 8 (FIGS. 4 and 7-8). Shoulder 16 contacts the periphery of lens 40 to prevent its longitudinal displacement relative to sled 4 during the contemplated movement.

Sled 4 and rod 5 are housed in the hollow interior 17 of support 2 in alignment with a longitudinal control aperture 18. Movement control means formed of a front sled control member 19 and a rear rod control member 20, individually longitudinally slidably received in interior 17, are correspondingly connected to the rear ends of sled 4 and rod 5, and provided with finger operated sled and rod tabs 21 and 22. Sled member 19 has a channel extension 19a (FIGS. 3-4) to accommodate slidably the rear portion of rod 5 which extends therethrough to reach rod member 20. Rear portion 6 has a removable end plug 23 (FIG. 1) for inserting the pertinent parts in interior 17. Sled member 19 may have separate mating top and bottom halves 19b and 19c to aid assembly of such parts and their insertion into interior 17.

Figure 9:
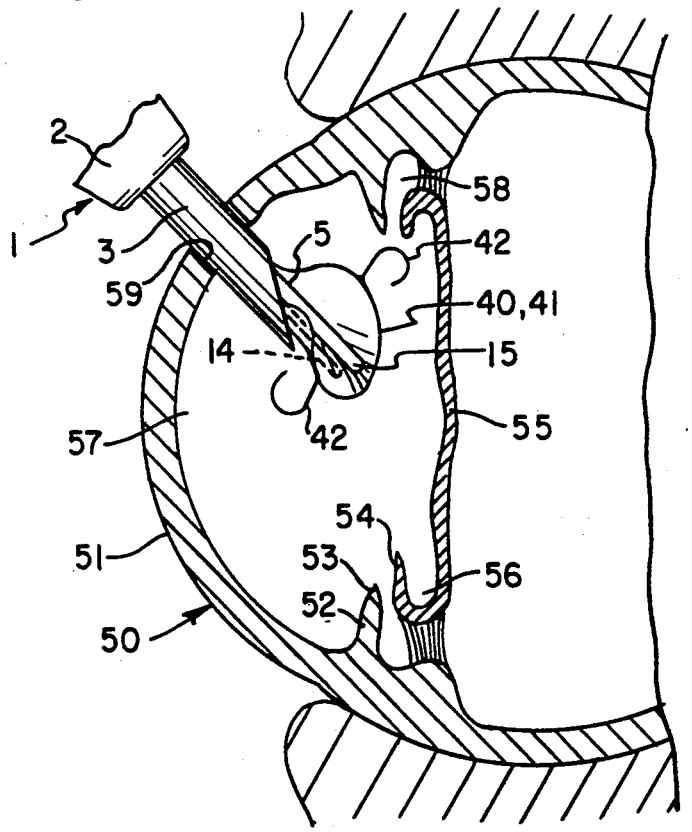
FIG. 9 is a schematic view showing the lens as it unfolds after injection of the tube insertion end into the eye.

Sled and rod members 19 and 20 control conjoint movement of sled 4 and rod 5 relative to tube 3 and individual movement of rod 5 relative to sled 4 and tube 3. A friction stop 24 in interior 17 is engaged by sled member 19 to denote a loading position of sled 4 at leading end 8 (FIG. 2), yet permits sled member 19 and rod member 20 to slide thereover in unison in moving sled 4 and rod 5 into loading end 8 to a contained position in tube 3 (FIGS. 4 and 8), and then out of insertion end 9 to an exposed position forwardly thereof after insertion end 9 has been inserted into the eye (FIG. 9).

Sled 4 and rod 5 are thus arranged on support 2 for movement relative to tube 3. Initially, sled member 19 is located behind stop 24 to place platform 14 of sled 4 at the loading position adjacent loading end 8 of tube 3, and rod member 20 is located rearwardly of sled member 19 to place tip 15 of rod 5 at a retracted position behind platform 14 (FIG. 6). At this point, lens 40 is loaded in unfolded state on platform 14 (FIGS. 1-2).

Using rod tab 22, rod member 20 is moved forward to abut sled member 19 and bring tip 15 to the loading position, thereby sliding tip 15 across lens 40 to lock it on platform 14 (FIG. 3).

Using sled tab 21 and rod tab 22, sled member 19 and rod member 20 are then moved in unison over stop 24 to move platform 14, lens 40 and tip 15 in unison from the loading position into loading end 8 to the contained position in bore 10, thereby gradually folding lens 40 into bore 10 and locating haptics 42 in top slot 11 so as to protrude to the exterior of tube 3, in controlled manner (FIGS. 4-5 and 7-8). At this point, injector 1 is ready to insert insertion end 9 in the eye incision.

While holding sled and rod tabs 21 and 22 stationary to prevent movement of sled and rod members 19 and 20 relative to support 2, and of sled 4, lens 40 and rod 5 relative to tube 3, injector 1 is inserted via insertion end 9 in the eye incision so that haptics 42 pass through the incision protruding from tube 3.

Once inserted, sled member 19 and rod member 20 are moved in unison, via tabs 21 and 22 as before, from the contained position (FIGS. 4-5 and 8) farther along interior 17, to move platform 14, lens 40 and tip 15 in unison out of insertion end 9 to the exposed position, thereby gradually unfolding lens 40 out of bore 10 and returning lens 40 and haptics 42 to unfolded state, in controlled manner. At this point, lens 40 is in the eye but still safely locked between platform 14 and tip 15 (FIG. 9).

Finally, while holding sled tab 21 stationary, rod tab 22 is moved rearwardly to retract rod member 20 from sled member 19 and move tip 15 back across unfolded lens 40 and away from platform 14 to unlock and release the lens, in controlled manner.

Thus, initially sled 4 is at the loading position at loading end 8 to load the unfolded lens 40 thereon, and rod 5 is at its retracted position to move to the loading position to lock the unfolded lens 40 to sled 4. Sled 4 and rod 5 then move in unison from the loading position into loading end 8 to the contained position in tube 3 to effect the lens folding and haptics locating action. On inserting insertion end 9 in the incision with haptics 42 freely protruding from slot 11, sled 4 and rod 5 move in unison from the contained position out of insertion end 9 to the exposed position to effect lens unfolding and lens and haptics return to unfolded state, whereupon rod 5 separately moves away from sled 4 to unlock and release the lens in the eye.

Loading end 8 forms an inclined end 25 defining a gradually constricting guide means for controlled gradual folding of lens 40 into bore 10 and controlled gradual guided locating of haptics 42 in top slot 11. Inclined end 25 tapers upwardly and inwardly along an incline from a distal longitudinal point 26 peripherally remote from slot 11 to a proximate longitudinal point 27 peripherally at slot 11. Also, insertion end 9 forms an inclined end 28 defining a gradually expanding guide means for controlled gradual unfolding of lens 40 out of bore 10 and controlled gradual return of lens 40 and haptics 42 to unfolded state. Inclined end 28 tapers downwardly and outwardly along an incline from a proximate longitudinal point 29 peripherally at slot 11 to a distal longitudinal point 30 peripherally remote from slot 11.

Inclined end 28 advantageously defines a pointed tip 31 for easy insertion of the front of tube 3 in the incision.

Opposed gradually constricting guide surfaces 32 are formed at loading end 8 to guide opposing peripheral portions of lens 40 gradually toward each other and conformingly against and into end 8 to aid in folding lens 40 as it moves thereinto. A breech recess 33 is defined in support 2 at surfaces 32 to locate unfolded lens 40 on platform 14. Opposed grooves 34 are formed at recess 33 to receive and locate the opposed haptics 42 in a direction crosswise of central top slot 11 to permit surfaces 32 to guide haptics 42 in predetermined orientation gradually upwardly toward each other and in turn longitudinally inwardly into slot 11 as lens 40 moves into loading end 8 (FIG. 7).

Tube 3 may have a restricted neck portion 35 extending rearwardly from the outer margin of loading end 8 under platform 14 (FIG. 6), to a tubular base portion 36, so that tube 3 is fixedly received along its extent in a nose portion 37 seated on front portion 7 of support 2. This construction enables tube 3 to be made of metal for easy assembly via nose portion 37 on support 2.

Rod 5, channel 13 and extension 19a, sled and rod members 19 and 20 and interior 17 are suitably of conforming cross sectional shape, e.g. circular, oval or polygonal shape. Desirably, tube 3, bore 10 and pin 15 are of circular cross sectional shape, platform 14 is of conforming arcuate shape, and tube 3 has a very thin wall thickness, to assure jam-free (non-binding) locking, moving, folding, unfolding and releasing of lens 40 (FIG. 5).

As shown in FIG. 9, the pertinent parts of the human eyeball 50 include the cornea 51, the iris 52 with its central opening or pupil 53, the remainder of the anterior lens capsule 54 after extracapsular removal of a cataracted natural lens, and the posterior lens capsule 55, so that posterior capsule 55 defines a cul-de-sac 56 at its peripheral margins that is formed between anterior and posterior capsules 54,55. The aqueous humor zone between cornea 51 and posterior capsule 55 is divided by iris 52 into an anterior chamber 57 and a posterior chamber 58.

Haptics 42 may seat in cul-de-sac 56, between anterior and posterior capsules 54,55, to position lens 40 so that lens body 41 performs its light focusing function.

Typically, lens body 41 has about a 5-6 mm diameter and 0.4 mm thickness, and haptics 42 have about a 0.2 mm thickness and 0.2 mm width. In undeformend state, haptics 42 may have about a 13 mm length from the outer edge of one haptic to the diametrically opposite outer edge of the other. As folded, lens body 41 may have about a 3 mm girth diameter, allowing its easy delivery in tube 3 of about like girth and with a wall thickness no larger than the lens body thickness, via an incision at most about 3.5 mm long. Lens body 41 is typically thinner at its edges, thus aiding their upward folding to center haptics 42 for entry into top slot 11 (FIG. 5).

As folded lens 40 is of bowed shape when loaded in bore 10, and as the diameter of bore 10 roughly equals the, e.g. about 3 mm, girth diameter of folded lens body 41, lens 40 moves via platform 14 and tip 15 easily through bore 10 without hindrance or damage. As haptics 42 protrude from slot 11, they are not affected by the moving, folding and unfolding actions of lens body 41 relative to tube 3, and avoid jamming of lens 40 in bore 10 during such actions. On inserting end 9 in the incision, haptics 42 easily slip therethrough without hindrance or damage.

Lens body 41 may be of any suitable temporarily resiliently deformable light focusing optic serving material that is sufficiently soft for the desired folding and also non-toxic and eye fluid compatible such as silicone, with haptics 42 typically being of slightly stiffer resiliently deformable material such as polypropylene. Lens body 41 must have a memory so that when folded to reduce its girth, it will return readily to unfolded state, so long as promptly inserted via the incision for unfolding in the eye, thus insuring against loss of such memory. The lens injection procedures are effected under sterile conditions.

The folding must occur during or just prior to surgery to avoid loss of "memory" of the lens as would occur if "folded" days or weeks before surgery. As used herein, "folding" means rolling, curling, gathering and like type compressing of lens body 41 around tip 15 for jam-free travel through bore 10.

Referring to FIG. 9, in order to inject lens 40, a minimum size corneal incision 59 is made by the surgeon, e.g. about 3.5 mm long, just sufficient to accept insertion end 9 of tube 3. Holding injector 1, loaded with lens 40 in bore 10, so that tube 3 is adjacent incision 59, insertion end 9 is inserted partially therein so as not to stress unduly incision 59, while at the same time sliding the protruding haptics 42 through the incision, e.g. at one end of the incision. Platform 14 and tip 15 are then gradually moved along bore 10 to unfold lens 40 out of insertion end 9, and tip 15 is retracted from platform 14 to release lens 40. Injector 1 is then removed from incision 59, whereupon forceps are used to seat lens 40 in the eye in the usual way.

Heretofore, when a tool was used to insert a folded lens, it fully occupied the incision along with the lens, causing patient trauma by stressing the incision or by increasing its size.

A conventional sterile, non-toxic lubricant liquid, which is compatible with the interior of the eye, may be applied to lens 40 and tube 3 to aid in folding and moving body lens 41 into and through bore 10 and in guiding haptics into and along slot 11.

As insertion end 9 projects inwardly of incision 59, the unfolding of lens 40 occurs without stressing the incision. Haptics 42 remain outside tube 3 throughout the folding, insertion, unfolding and lens releasing procedures, thus avoiding friction jamming of lens body 41 and haptics 42 in tube 3 as could occur if haptics 42 were also contained in bore 10. This jamming would prevent free movement of lens 40 relative to tube 3 when insertion end 9 is in the eye, exposing the patient to trauma, and lens body 41 and haptics 42 to structural damage.

As haptics 42 remain outside tube 3, lens body 41 is more easily folded into bore 10. Grooves 34 locate haptics 42 in a predetermined orientation and surfaces 32 guide them upwardly toward each other to enter slot 11 at a corresponding predetermined location. Although they protrude from slot 11, haptics 42 are of such small thickness as to slip easily through incision 59 without stressing it or causing patient trauma. As lens 40 unfolds from insertion end 9, haptics 42 are spaced safely from cornea 51 to avoid touching it as they return to expanded state. The lateral location of the haptics 42 relative to central slot 11 is predetermined, and insertion end 9 projects sufficiently into the eye for proximate point 29 to clear incision 59. On moving to exposed position, lens 40 clears insertion end 9 as it unfolds, spacing the laterally oriented haptics 42 from cornea 51 by the combined distance of the inserted part of insertion end 9 and at least the radius of lens 40 (FIG. 9).

Injector 1 injects lens 40 into the eye while inserting tube 3 only partially in incision 59. Forceps are only used to seat lens 40 in the eye after removing tube 3 from incision 59, thus avoiding stress on the incision. As lens 40 is controlled by the gradual movements of insertion end 9, sled 4 and rod 5, it is gradually injected, gradually unfolded and gradually released, in controlled manner, preventing it from bursting open from folded state, or from being released, in uncontrolled manner. The procedure safely avoids contact of the unfolding or released lens and protruding haptics with cornea 51 or other eye parts.

Injector 1 facilitates exploitation of the minimum size incision used for extracapsular removal of the natural lens, as insertion end 9 may be partially inserted in that same incision to inject lens 40 into the eye. This is significant as the smaller the incision size the less the patient trauma, including pain and discomfort then and later, not only due to the incision itself but also to the number and/or size of any needed sutures.

Referring to FIGS. 10-11, a modified tube 3' construction is shown having the same parts as tube 3, including neck portion 35 and base portion 36, plus nose portion 37, but differing therefrom in that tube 3' is made of plastic while tube 3 is made of metal. Tube 3' is an integral element in which the corresponding tube proper, neck portion, base portion and nose portion form a low cost fabricated, selectively shaped one-piece construction.

In general, support 2, tube 3 or 3', sled 4 and rod 5 may be of any suitable non-toxic material, e.g. metal or rigid plastic such as Teflon. Clearly, the parts of the injector of the invention are structurally simple, readily fabricated at relatively low cost, and may be provided as disposable parts.

The specification and drawings are for illustration and not limitation, and may be modified without departing from the invention which is limited solely by the scope of the claims.

What is claimed is:

1. Slotted tube injector for partial insertion in a minimum size eye incision to inject into the eye a temporarily folded intraocular lens having generally opposed seating haptics extending from the lens periphery, comprising a longitudinal support forwardly terminating in a tube having a rearwardly facing loading end and a forwardly facing insertion end interconnected by a through bore to contain the folded lens, and a slot extending from the loading end to the insertion end and communicating the bore with the exterior of the tube to permit the haptics to protrude to the exterior from the folded lens in the bore, the insertion end being insertable in the incision, and holding and locking means arranged on the support for movement relative to the tube for loading and locking the lens in unfolded state thereon at the loading end, for moving the lens into the loading end for controlled folding of the lens into the bore and locating of the haptics in the slot so as to protrude to the exterior, and upon inserting the insertion end in the incision with the haptics passing through the incision protruding from the tube, for moving the lens out of the insertion end for controlled unfolding of the lens out of the bore and return of the lens and haptics to unfolded state thereon, and for unlocking the unfolded lens for controlled release therefrom in the eye.

2. Injector of claim 1 wherein gradually constricting guide means are provided at the loading end for controlled gradual folding of the lens into the bore and locating of the haptics in the slot.

3. Injector of claim 2 wherein the constricting guide means are defined by an inclined loading end which tapers upwardly and inwardly along an incline from a distal longitudinal point peripherally remote from the slot to a proximate longitudinal point peripherally at the slot.

4. Injector of claim 1 wherein gradually expanding guide means are provided at the insertion end for controlled gradual unfolding of the lens out of the bore and return of the lens and haptics to unfolded state.

5. Injector of claim 4 wherein the expanding guide means are defined by an inclined insertion end which tapers downwardly and outwardly along an incline from a proximate longitudinal point peripherally at the slot to a distal longitudinal point peripherally remote from the slot.

6. Injector of claim 5 wherein the inclined insertion end defines a pointed tip for insertion in the incision.

7. Injector of claim 1 wherein the holding and locking means include a holding sled and a locking rod arranged on the support for movement relative to the tube for loading the lens in unfolded state on the sled and locking it thereto by the rod at the loading end, for moving the sled and rod into the loading end for said lens folding and haptics locating, and upon said inserting of the insertion end in the incision, for moving the sled and rod out of the insertion end for said lens unfolding and lens and haptics return to unfolded state, and for moving the rod away from the sled for unlocking the lens for said release.

8. Injector of claim 7 wherein the sled is arranged initially at a loading position at the loading end for loading the lens in unfolded state thereon, the rod is arranged initially at a retracted position for moving to the loading position to lock the lens to the sled, the sled and rod are movable from the loading position into the loading end to a contained position in the tube for said lens folding and haptics locating , and upon said inserting of the insertion end in the incision, the sled and rod are movable from the contained position out of the insertion end to an exposed position for said lens unfolding and lens and haptics return to unfolded state, and the rod is separately movable away from the sled for said lens unlocking and release.

9. Injector of claim 7 wherein opposed gradually constricting guide surfaces are provided at the loading end to guide opposing peripheral portions of the lens gradually toward each other and conformingly against and into the loading end for folding the lens during movement into the loading end.

10. Injector of claim 9 wherein a breech recess is defined in the support at the guide surfaces to locate the unfolded lens on the sled, and opposed grooves are provided at the recess to receive and locate the opposed haptics in a direction crosswise of the slot to permit the guide surfaces to guide the haptics in predetermined orientation gradually toward each other and in turn longitudinally inwardly into the slot during lens movement into the loading end.

11. Injector of claim 7 wherein the sled comprises a longitudinal body having a rearward channel slidably receiving the rod coaxially to the bore of the tube, and a forward platform to load the lens thereon, the rod having a forward tip for overlying registry with the platform, and the platform being transversely offset from the channel a distance corresponding substantially to the thickness of the unfolded lens to enable the tip to move into registry with the platform to lock the lens therebetween for folding the lens generally coaxially around the tip as a core during movement into the loading end.

12. Injector of claim 11 wherein the platform has a shoulder for contacting the lens periphery to prevent longitudinal lens displacement relative to the sled during said movement.

13. Injector of claim 7 wherein movement control means are provided on the support for controlling conjoint movement of the sled and rod relative to the tube and individual movement of the rod relative to the sled and tube.

* * * * *